United States Patent
Boese et al.

(10) Patent No.: US 7,620,441 B2
(45) Date of Patent: Nov. 17, 2009

(54) METHOD AND DEVICE FOR IMPROVED ECG TRIGGERING

(75) Inventors: Jan Boese, Eckental (DE); Johann Seissl, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 496 days.

(21) Appl. No.: 11/455,263

(22) Filed: Jun. 16, 2006

(65) Prior Publication Data

US 2006/0287594 A1    Dec. 21, 2006

(30) Foreign Application Priority Data

Jun. 16, 2005    (DE) .................. 10 2005 027 944

(51) Int. Cl.
*A61B 5/0452*    (2006.01)
*A61B 5/05*    (2006.01)
(52) U.S. Cl. ...................... 600/413; 600/428
(58) Field of Classification Search ............ 600/413, 600/428
See application file for complete search history.

(56) References Cited

U.S. PATENT DOCUMENTS

| | | | |
|---|---|---|---|
| 6,210,333 B1 * | 4/2001 | Gardner et al. | 600/450 |
| 2004/0176681 A1 * | 9/2004 | Mao et al. | 600/413 |
| 2005/0090737 A1 * | 4/2005 | Burrell et al. | 600/428 |

FOREIGN PATENT DOCUMENTS

WO    WO 97/47237 A1    12/1997

OTHER PUBLICATIONS

Bin Lu, Nan Zhuang, Song-Shou Mao, Janis Child, Sivi Carson, Matthew J. Budoff, "Baseline Heart Rate-adjusted Electrocardiographic Triggering for Coronary Artery Electron-Beam CT Angiography", Radiology, Nov. 2004, pp. 590-595, vol. 233, No. 2.

* cited by examiner

*Primary Examiner*—George R Evanisko
*Assistant Examiner*—Andrew Hayes

(57) ABSTRACT

The invention relates to a method and a device for improved imaging by means of ECG triggering. A first trigger time A and a second trigger time B, as well as a threshold value for the heart rate variability is determined with the method according to the invention. The heart rate variability is subsequently calculated. Trigger time A is used as long as the threshold value is exceeded. Trigger time B is used when the threshold value is reached or exceeded.

19 Claims, 2 Drawing Sheets

METHOD AND DEVICE FOR IMPROVED ECG TRIGGERING

CROSS REFERENCE TO RELATED APPLICATIONS

This application claims the benefits of German Patent application No. 10 2005 027 944.9 filed Jun. 16, 2005 and is incorporated by reference herein in its entirety.

FIELD OF THE INVENTION

The invention relates to a method and a device for improved ECG triggering.

BACKGROUND OF THE INVENTION

Imaging methods for displaying the heart are known in the prior art, by means of fluoroscopy, ultrasound, computed tomography (CT) or magnetic resonance (MR) for example.

If the heart is to be displayed by means of imaging methods, it is generally necessary to account for the movement of the heart. One possibility for this is the so-called ECG triggering. The recording of an image is triggered here by a time derived from the ECG signal (electrocardiogram signal). The so-called R wave is typically used as the characteristic feature in the ECG. The trigger time is then defined either as an absolute time after the R wave (e.g. 400 ms after the R wave) or as a percentage value of the RR interval.

On the one hand, consecutive images of the same heart phase can be generated in this way, (e.g. with fluoroscopy, ultrasound imaging), on the other hand raw data relating to a number of heart beats and necessary for the reconstruction of an image can be picked (e.g. with CT or MR imaging). The trigger time is typically selected such that the structure to be imaged moves as little as possible during the recording window.

One problem with ECG triggering is the fluctuation of the heart rate. It thus results in a time defined on the basis of the ECG (e.g. 200 ms after the R wave or 50% of the RR interval) not always corresponding to the same mechanical heart phase if the heart rate is not constant. One example of this is shown in FIG. 1. With a trigger time of 50% of the RR interval, the trigger time normally falls mid interval. This is clarified by triggers 1 and 2 characterized by arrows 1 and 2. With an erratic increase in the heart rate, the trigger time, which was calculated on a heart rate, which corresponds to the first two intervals shown, can fall within a completely unsuitable heart phase (see trigger 3).

Different approaches to optimizing the ECG triggering, which aim to adjust the trigger times to the heart rate exist in the prior art, see for instance Lu B, Zhuang N, Mao S S, Child J, Carson S, Budoff M J. "Baseline heart rate-adjusted electrocardiographic triggering for coronary artery electron-beam CT angiography" Radiology (2004) November; 233 (2):590-5. Reference is made in this article to an ECG triggering which was adjusted to the baseline heart rate and which delivers better results in comparison with a conventional ECG triggering of 80%. However, here too the problem is not solved whereby during the recording of a fluctuating heart rate, the trigger times can fall within unsuitable heart phases. The authors of the said publication thus themselves point out in their discussion that an ECG triggering adjusted to the baseline heart rate is also a problem for patients with cardiac arrhythmia.

In the prior art, further attempts were made to minimize this problem, in which trigger times were used which are positioned closer to the R wave. By way of example, a trigger time of 10% is clearly less dependent on heart rate fluctuations than the time of 50% used in FIG. 1. This solution is however unsuitable for some clinical applications, since subsequent trigger times (such as 90% for instance) are here preferable because the structure to be imaged in this heart phase is as still as possible.

SUMMARY OF THE INVENTION

The object underlying this invention is thus to provide an improved method, which at least partially eliminates the said problems relating to the trigger times.

This object is achieved in accordance with the invention by a method according to the claims.

DETAILED DESCRIPTION OF THE INVENTION

Figure 1:
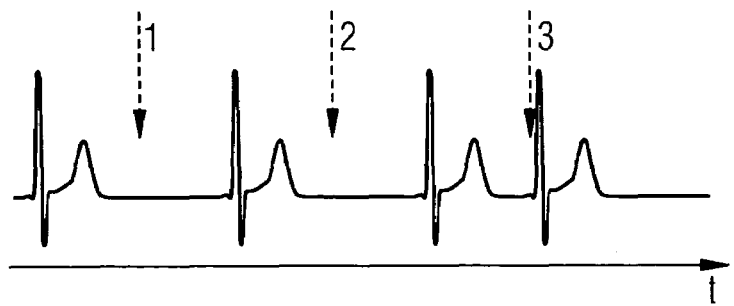
FIG. 1 shows an example of a triggering problem.

The basic concept of this invention is to change between different trigger strategies as a function of the heart rate variability.

The following steps are thus carried out in detail:
Providing an ECG with n heart beat intervals,
Determining a first trigger time A and a second trigger time B as well as a threshold value for the heart rate variability,
Calculating the heart rate variability on the basis of the n heart beat intervals,
Implementing the ECG triggering for the imaging using the trigger time A to trigger a recording, with a changeover to the trigger time B being carried out when the threshold value for the heart rate variability is reached or exceeded.

ECG data is firstly provided, which features a number n of heart beat intervals, and thus displays a certain time window. This time window can be created even before the actual ECG triggering and can be used for the calculations. It is however also possible to begin already with the imaging method by means of triggering using the previously determined trigger times, and to collect the ECG data during the triggering. It is then possible to calculate the heart rate or/and the heart rate variability during the imaging in updated time windows. If necessary, this procedure then allows the trigger times A or/and B and if necessary further trigger times to be re-determined. It is likewise possible to adjust the threshold value/s for the heart rate variability.

Instead of constantly adjusting the selection of trigger time A or B or of the threshold value for the heart rate variability, it can however also be useful to carry out this decision as a one off shortly before the start of an image recording session and to retain the decision right up to the end.

The trigger times A and B are preferably determined. It is however also possible to additionally determine further trigger times.

Trigger time A is the optimum time for the imaging with constant heart rate. In accordance with the invention, trigger time values in a range of approximately 40% to 98%, in particular approximately 45%, 50%, 55%, 60%, 65%, 70%, 75%, 80%, 85%, 90%, 95% or 98% are particularly preferable here. Such values are particularly preferably here, which are set to an optimum still phase of the object to be imaged. Potential trigger problems need not be taken into account here. This trigger time is used with a patient with a relatively constant heart beat.

The precise determination of the trigger time depends on the respective imaging type and can be carried out by a person skilled in the art without any problem.

By way of example, a triggering shortly before the R wave (e.g. 95%) is ideal for the imaging of the left ventricle by means of fluoroscopy.

Alternatively, the trigger times are also determined as absolute values. Values of 200 ms to 500 ms are suitable for A for instance. However, the precise values depend on the heart rate of the subject to be examined.

It is also possible to use values which represent a time prior to the R wave, e.g. A=−100 ms for the trigger time A. Preferred values thus lie in the range of −150 ms to −10 ms, e.g. −50 ms etc.

Furthermore, a trigger time B is determined, which is used if a secure triggering with time A is not expedient as a result of a high heart rate variability. Trigger time B is either determined at the start, or is only determined after the heart rate variability definition has been calculated.

A trigger time is preferably selected for B, which also does not fall within a completely unsuitable heart phase when heart rate fluctuations occur. B thus preferably lies in a region which is as independent as possible from heart rate fluctuations. This region preferably lies around the R wave, preferably on the R wave or shortly thereafter.

If a time is selected for A, which sets a trigger to an optimum still phase of the heart, time B is in this case preferably earlier than time A, e.g. B=20%. Values of 3% to 50% are preferable here, preferably 5% to 30%, preferably 5% to 25%, preferably 5% to 20%, preferably 5% to 15%, preferably 5% to 10%.

In the case of patients with significant fluctuations in the heart rate, triggering can be with the R wave directly, this not however corresponding to the optimum still phase, but always functioning reliably. B can also be set to a trigger time shortly after the R wave.

Two threshold values can also be determined for heart rate fluctuations, as well as two associated trigger times for B. If a heart rate fluctuation occurs which lies in a certain region, trigger time B is used, e.g. B=20%. If an even more significant heart rate fluctuation occurs, a further trigger time is used, e.g. trigger with R wave.

Alternatively, B can also be determined as an absolute value, e.g. B=10 ms. The values for B preferably lie in the range of 5 ms to 150 ms.

The invention thus allows a compromise to be found between optimum heart phases for the imaging and the stability of the triggering. Whilst the optimum heart rate is used with a stabile heart rate, with a non-stable heart rate, the optimum time is dispensed with, but a stable triggering is however achieved.

It is thus irrelevant whether the heart rate variability means that the heart rate increases or reduces. The system according to the invention is able to change over to using the trigger time B if any change in the heart rate occurs.

Furthermore, A and B can both be automatically adjusted to the current heart rate, as described in Lu B, Zhuang N, Mao S S, Child J, Carson S, Budoff M J. "Baseline heart rate-adjusted electrocardiographic triggering for coronary artery electron-beam CT angiography" Radiology (2004) November; 233(2):590-5.

Furthermore, a threshold value is determined for the heart rate variability.

If further trigger times are additionally determined at B, additional threshold values are determined for the additional trigger points.

The ECG signal of the subject to be examined is preferably continuously evaluated prior to or/and during the recording. A time window over n heart beat intervals is analyzed here and a measure is determined for the heart rate variability, which specifies to what degree the heart rate fluctuates.

In one possible implementation, the average quadratic deviation SDRR of the RR intervals is determined here by its mean value:

$$RR_{mean} = \frac{1}{n}\sum_{i=1}^{n} RR_i$$

with $RR_i$ being consecutive heart beat intervals and n being the number of intervals used for the analysis.

$$SDRR = \sqrt{\frac{1}{n-1}\sum_{i=1}^{n}(RR_i - RR_{mean})^2}$$

A typical value of n lies in the range of 3 to 20, preferably 5 to 15, preferably 5 to 10, preferably 6 to 8.

By using SDRR as a variability measure, threshold values preferably lie between 10 ms and 200 ms (milliseconds), with values such as 30 ms, 50 ms, or 100 ms preferably being used.

Aside from SDRR, other variability measures are however also possible.

A trigger time is selected as a function of a previously determined variability threshold value.

Trigger time A is normally used. However, if the heart rate variability reaches or exceeds the threshold value, trigger time B is used.

The selected trigger time is used to trigger the recording.

With this method, the heart rate variability is preferably continuously measured on the basis of current time windows with n heart beat intervals in each instance. The heart rate variability is re-measured after each triggering and the trigger time is thus selected anew.

Alternatively, the trigger mode can also be changed over with a certain "inertia", i.e. a changeover into Mode B is not carried out until after a specific time with a high heart rate variability, and only when a low heart rate variability is present over a further specific time is a changeover carried out back into Mode A.

A further subject matter of the present invention is a device for implementing the above-described method. The invention particularly relates to a device for the imaging by means of ECG triggering, comprising a device for recording an ECG with n heart beat intervals, a data processing device, with a first trigger time A, a second trigger time B, as well as a threshold value for the heart rate variability being stored in the data processing device, a device for calculating the heart rate variability on the basis of n heart beat intervals, a device for implementing the ECG triggering using the trigger time A, with the trigger time B being used when the threshold value for the heart rate variability is reached or exceeded.

The device is suitable for implementing the above-described method with the described features.

FIG. 1 shows an example of a triggering problem. An ECG with a number of heart beats is displayed. The arrows characterized with 1, 2, and 3 each represent a trigger for the recording of an image. The trigger time lies at 50% of the RR interval. An erratic change in the heart rate causes trigger 3 to fall within a heart phase as trigger 1 and 2.

Figure 2:
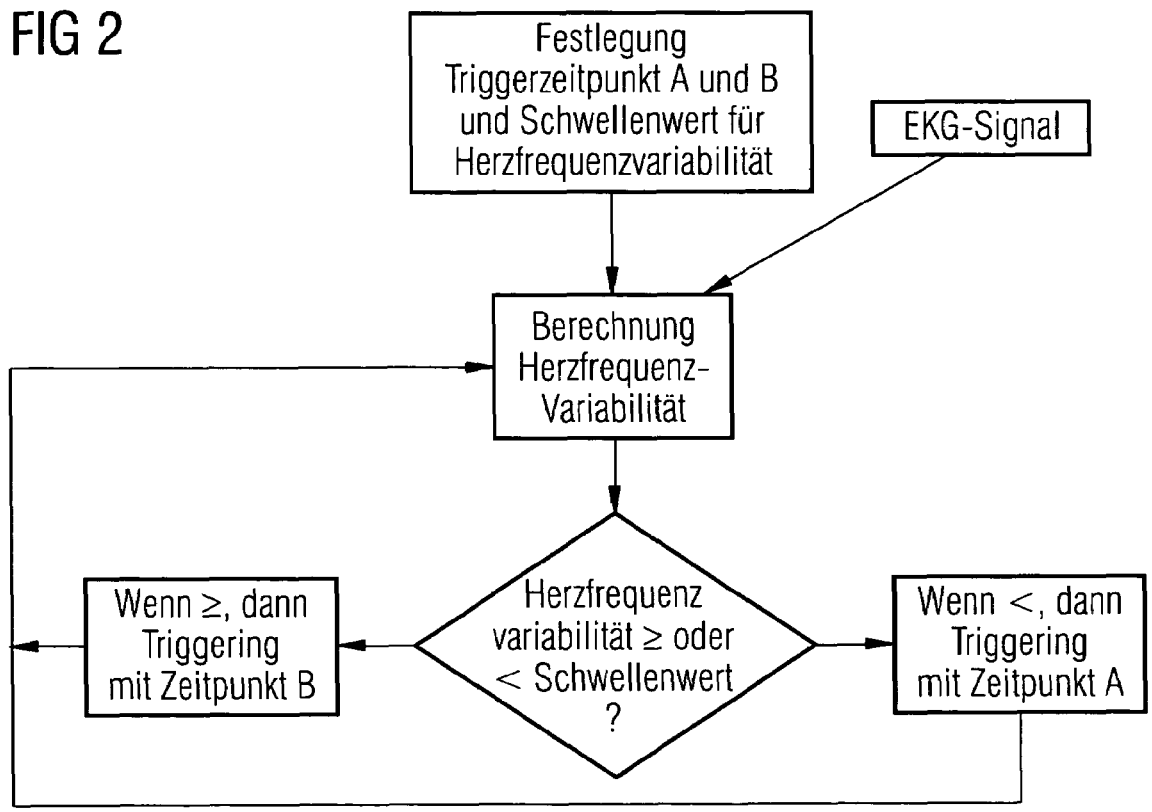
FIG. 2 shows a flow diagram which illustrates an embodiment of the method of the present invention.

FIG. 2 shows a flow diagram which illustrates an embodiment of the method of the present invention:

Trigger times A and B are first determined. A threshold value for the heart rate variability is likewise determined. The heart rate variability is subsequently calculated using the ECG with n heart beat intervals. If the heart rate variability is smaller than the threshold value, trigger time A is used for the imaging. If the heart rate variability is identical to or greater than the threshold value, trigger time B is used for the imaging. The heart rate variability is recalculated after each decision for the trigger time, and the trigger time is in turn selected.

Figure 3:
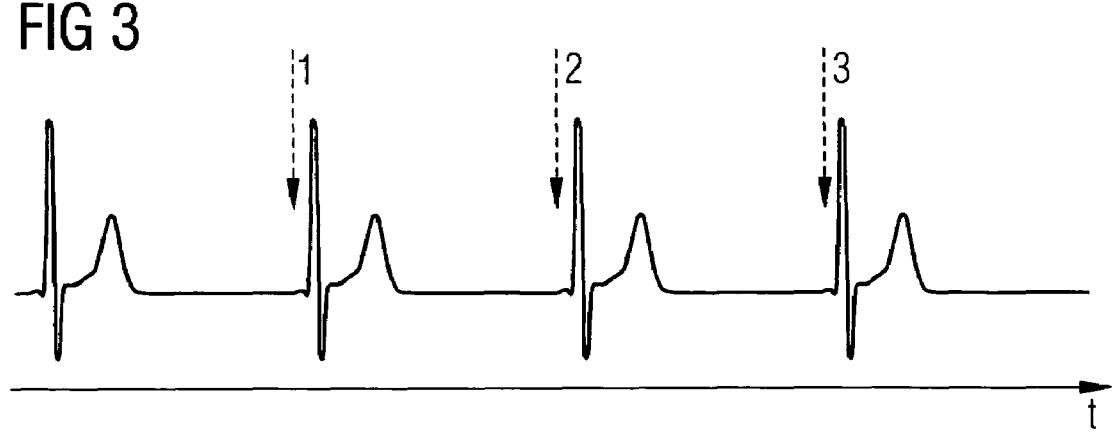
FIG. 3 shows the case in which the heart rate variability is smaller than the threshold value.

FIG. 3 shows the case in which the heart rate variability is smaller than the threshold value. Trigger time A is used. In this case, A-95% is determined.

Figure 4:
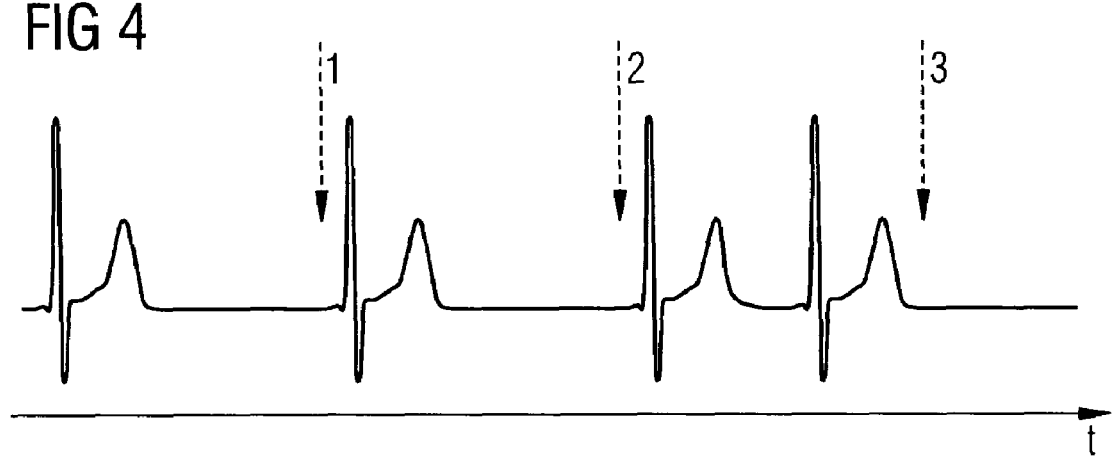
FIG. 4 shows the case in which the use of trigger time A (A=95%) with a high heart rate variability would lead to false triggers (see trigger 3).

FIG. 4 shows the case in which the use of trigger time A (A=95%) with a high heart rate variability would lead to false triggers (see trigger 3). This case is avoided by the method according to the invention.

Figure 5:
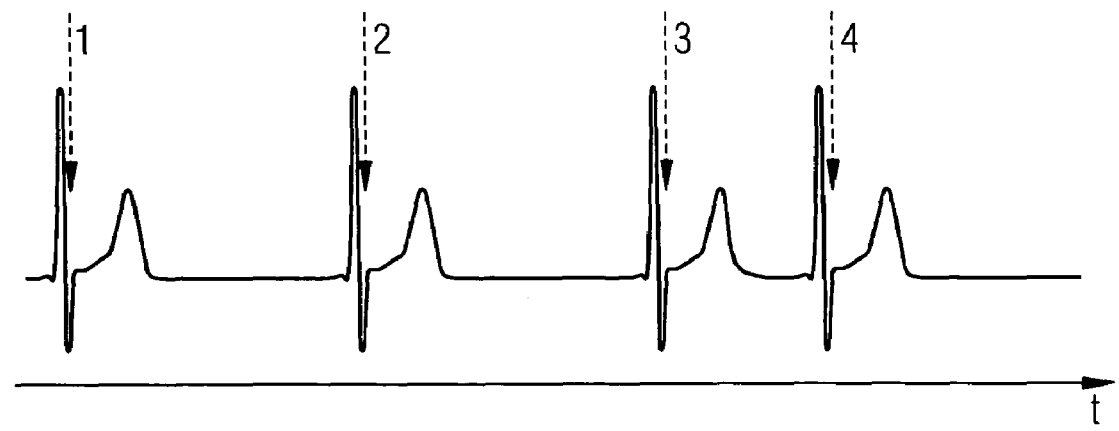
FIG. 5 shows the case in which the heart rate variability is greater than the threshold value.

FIG. 5 shows the case in which the heart rate variability is greater than the threshold value. In accordance with the present invention, trigger time B=5% is used.

The invention claimed is:

1. A method for ECG triggering of imaging recording, comprising:
    recording an ECG with a plurality of heart beat intervals;
    determining a first trigger time and a second trigger time and a heart rate variability threshold value;
    calculating a heart rate variability based on a plurality of recorded heart beat intervals;
    initiating ECG imaging recording based on the first trigger time and changing recording initiation to the second trigger time when the heart rate variability threshold value is reached or exceeded.

2. The method according to claim 1, further comprising repeating the steps of calculating the heart rate variability and initiating ECG imaging recording based on the first trigger time and changing recording initiation to the second trigger time when the heart rate variability threshold value is reached or exceeded.

3. The method according to claim 2, wherein the first trigger time is determined so that it coincides within an optimum still phase of the heart.

4. The method according to claim 3, wherein the second trigger time is determined to coincide with an R wave or shortly after.

5. The method according to claim 4, wherein the heart rate variability is calculated by using an average quadratic deviation SDRR of an RR interval from a mean value according to:

$$SDRR = \sqrt{\frac{1}{n-1} \sum_{i=1}^{n} (RR_i - RR_{mean})^2},$$

where:

$$RR_{mean} = \frac{1}{n} \sum_{i=1}^{n} RR_i$$

and:
    n is the number of heart beat intervals,
    R is the R wave,
    $RR_i$ is consecutive heart beat intervals, and
    $RR_{mean}$ is the average value of $RR_i$.

6. The method according to claim 5, wherein the number of heart beat intervals is between 3 to 20.

7. The method according to claim 6, wherein, the number of heart beat intervals is between 5 to 15.

8. The method according to claim 7, wherein, the number of heart beat intervals is between 5 to 10.

9. The method according to claim 8, wherein the heart rate variability is continually recalculated and the first and second trigger times are redetermined based on the recalculated heart rate variability.

10. The method according to claim 9, wherein the second trigger time is only used after reaching or exceeding the heart rate variability threshold value after a temporal delay.

11. A device for ECG triggering of imaging recording, comprising:
    an ECG recording device that records an ECG with a plurality of heart beat intervals;
    a data processing device having a first trigger point, a second trigger point and a heart rate variability threshold value stored in the data processing device;
    a heart rate variability calculator that calculates heart rate variability based on the plurality of recorded heart beat intervals; and
    an ECG triggering device that initiates ECG imaging recording based on the first trigger point and changes recording initiation to the second trigger point when the heart rate variability threshold value is reached or exceeded.

12. The device according to claim 11, wherein the first trigger point is determined so that it coincides within an optimum still phase of the heart.

13. The device according to claim 12 wherein the second trigger point is determined to coincide with an R wave.

14. The device according to claim 13, wherein the heart rate variability is calculated by using an average quadratic deviation SDRR of an RR interval from a mean value according to:

$$SDRR = \sqrt{\frac{1}{n-1} \sum_{i=1}^{n} (RR_i - RR_{mean})^2},$$

where:

$$RR_{mean} = \frac{1}{n}\sum_{i=1}^{n} RR_i$$

and:
- n is the number of heart beat intervals,
- R is the R wave,
- $RR_i$ is consecutive heart beat intervals, and
- $RR_{mean}$ is the average value of $RR_i$.

15. The device according to claim 14, wherein the number of heart beat intervals is between 3 to 20.

16. The device according to claim 15, wherein, the number of heart beat intervals is between 5 to 15.

17. The device according to claim 16, wherein, the number of heart beat intervals is between 5 to 10.

18. The device according to claim 17, wherein the heart rate variability is continually recalculated and the first and second trigger points are redetermined based on the recalculated heart rate variability.

19. The device according to claim 18, wherein the second trigger point is only used after reaching or exceeding the heart rate variability threshold value after a temporal delay.

* * * * *

UNITED STATES PATENT AND TRADEMARK OFFICE
CERTIFICATE OF CORRECTION

PATENT NO.       : 7,620,441 B2                                    Page 1 of 1
APPLICATION NO.  : 11/455263
DATED            : November 17, 2009
INVENTOR(S)      : Boese et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 650 days.

Signed and Sealed this

Twenty-sixth Day of October, 2010

David J. Kappos
*Director of the United States Patent and Trademark Office*